US010473574B2

(12) United States Patent
Di Cagno et al.

(10) Patent No.: US 10,473,574 B2
(45) Date of Patent: Nov. 12, 2019

(54) ASSEMBLY FOR ASSESSING DRUG PERMEABILITY WITH ADJUSTABLE BIOMIMETIC PROPERTIES

(71) Applicant: Syddansk Universitet, Odense M (DK)

(72) Inventors: Massimiliano Pio Di Cagno, Tromsø (NO); Annette Bauer-Brandl, Odense (DK)

(73) Assignee: Syddansk Universitet, Odense M (DK)

( * ) Notice: Subject to any disclaimer, the term of this patent is extended or adjusted under 35 U.S.C. 154(b) by 234 days.

(21) Appl. No.: 15/525,526

(22) PCT Filed: Nov. 17, 2015

(86) PCT No.: PCT/DK2015/050352
§ 371 (c)(1),
(2) Date: May 9, 2017

(87) PCT Pub. No.: WO2016/078667
PCT Pub. Date: May 26, 2016

(65) Prior Publication Data
US 2018/0031465 A1 Feb. 1, 2018

(30) Foreign Application Priority Data

Nov. 17, 2014 (DK) ................................ 2014 70708
Apr. 29, 2015 (DK) ................................ 2015 70253

(51) Int. Cl.
G01N 15/08 (2006.01)
G01N 33/15 (2006.01)

(52) U.S. Cl.
CPC ......... G01N 15/08 (2013.01); G01N 15/0806 (2013.01); G01N 15/0826 (2013.01); G01N 33/15 (2013.01)

(58) Field of Classification Search
None
See application file for complete search history.

(56) References Cited

U.S. PATENT DOCUMENTS 4,927,879 A * 5/1990 Pidgeon ................. A61K 9/127
              210/656
6,936,699 B2 * 8/2005 Peters ....................... C07K 1/34
              435/69.1

(Continued)

FOREIGN PATENT DOCUMENTS

EP        1779921 A1    5/2007
WO   WO 2014/063097    4/2014

OTHER PUBLICATIONS

Amidon et al.: "A Theoretical Basis for a Biopharmaceutic Drug Classification: The Correlation of in Vitro Drug Product Dissolution and in Vivo Bioavailability". Pharmaceutical Research (1995), 12(3), pp. 413-420.

(Continued)

Primary Examiner — Paul M. West
Assistant Examiner — Mark A Shabman
(74) Attorney, Agent, or Firm — Knobbe, Martens, Olson & Bear, LLP

(57) ABSTRACT

There is provided an assembly and process for its preparation for predicting the permeability of chemical compounds, comprising a donor compartment for adding a composition comprising the compound; a barrier based on a support and a phospholipid layer adhering to the support; and an acceptor compartment for accepting the compound upon permeation of the barrier.

20 Claims, 6 Drawing Sheets

(56) References Cited

U.S. PATENT DOCUMENTS

| | | | | |
|---|---|---|---|---|
| 2003/0219716 A1* | 11/2003 | Avdeef | ................ | G01N 13/00 |
| | | | | 435/4 |
| 2007/0181490 A1* | 8/2007 | Chen | ................ | B01D 61/38 |
| | | | | 210/500.27 |
| 2011/0250659 A1* | 10/2011 | Roberts | ................ | C12N 9/20 |
| | | | | 435/134 |
| 2012/0152841 A1 | 6/2012 | Vissing et al. | | |

OTHER PUBLICATIONS

Corti et al.: "Development and evaluation of an in vitro method for prediction of human drug absorption. I. Assessment of artificial membrane composition." European Journal of Pharmaceutical Sciences, vol. 27, Issue 4, Mar. 2006, pp. 346-353.

Engesland et al.: "New Applications of Phospholipid Vesicle-Based Permeation Assay: Permeation Model Mimicking Skin Barrier", Journal of Pharmaceutical Sciences, 2013, vol. 102, Issue 5, pp. 1588-1600.

Fischer et al.: "Application of simulated intestinal fluid on the phospholipid vesicle-based drug permeation assay." International Journal of Pharmaceutics, vol. 422, Issues 1-2, Jan. 2012, pp. 52-58.

Flaten et al.: "Drug permeability across a phospholipid vesicle based barrier: A novel approach for studying passive diffusion", European J. Pharm. Sci., 2006, 27: 80-90.

Hidalgo et al.: Characterization of the Human Colon Carcinoma Cell Line (Caco-2) as a Model System for Intestinal Epithelial Permeability, Gastroenterology, 1989, 96: pp. 736-49.

Ingels et al.: "Effect of simulated intestinal fluid on drug permeability estimation across Caco-2 monolayers." International Journal of Pharmaceutics, vol. 274, Issues 1-2, Apr. 2004, pp. 221-232.

Naderkhani et al.: "Development of a Biomimetic Phospholipid Vesicle-based Permeation Assay for the Estimation of Intestinal Drug Permeability." Journal of Pharmaceutical Sciences, Jun. 2014, vol. 103, Issue 6, pp. 1882-1890.

* cited by examiner

ASSEMBLY FOR ASSESSING DRUG PERMEABILITY WITH ADJUSTABLE BIOMIMETIC PROPERTIES

CROSS REFERENCE TO RELATED APPLICATIONS

This application is a U.S. National Phase Application of PCT International Application Number PCT/DK2015/050352, filed on Nov. 17, 2015, designating the United States of America and published in the English language, which is an International Application of and claims the benefit of priority to Danish Patent Application No.: PA 2014 70708, filed on Nov. 17, 2014 and Danish Patent Application No.: PA 2015 70253, filed Apr. 29, 2015. The disclosures of the above-referenced applications are hereby expressly incorporated by reference in their entireties.

FIELD OF THE INVENTION

The present invention is directed to biomimetic barriers, such as cellulose hydrate foil supports coated with a mixture of phospholipids and additives. More specifically, the invention is directed to a permeation assay involving such modified barriers.

BACKGROUND OF THE INVENTION

The measurement of physicochemical properties, such as permeability, in a high-throughput screening environment plays an important role in the selection of the most promising biologically active molecules for lead optimization in pharmaceutical and biotechnological research and development, and in identifying active compounds with suitable distribution properties in agrochemical research and development.

In pharmaceutical research, the search for new chemical entities potentially useful as drugs takes place in three stages: exploration, discovery, and development. In the first stage, a therapeutic target is selected, and a biological screening assay developed. In the course of a year at a large pharmaceutical company, it is not uncommon to have 100,000 to 1,000,000 library compounds tested against a particular target. Of the molecules tested for biological activity, about 3000 to 10,000 are found to be active (hits). The initial part of the discovery step is called "lead" generation, where the most promising subset of the hits is selected for further testing. The selection of leads takes into account biopharmaceutic properties of the hits, such as measured aqueous solubility, octanol-water partition coefficients, plasma stability, human serum protein binding, cytochrome P450 inhibition (oxidative metabolism), liver microsome assay (general metabolism), and membrane permeability. These various tests filter out many molecules with unfavorable bio-pharmaceutic ADME properties (absorption, distribution, metabolism, and excretion).

ADME is the single largest cause of attrition in drug development. Methods, which can lower this high attrition rate, would benefit the industry by reducing failure rates; the pharmaceutical companies by reducing costs; and consumers by helping to get better drugs to market, in less time.

One of the common problems observed with new entities is the ability to overcome biological barriers, e.g. entering the blood circulation from the gastro-intestine or to enter the interior of a cell. This ability is routinely assessed, because it is an important pre-requisite for any substance to be transported to the site of possible pharmacological action. Decisions about the ability to develop new molecular entities are made based on such experiments. Moreover, the FDA (US Food and Drug Administration) has acknowledged the biopharmaceutical classification system [1], which has made it possible to reduce the extent of formulation work in the drug development phase, which is necessary for the registration of new drug preparations. The decision is based on solubility and permeability experiments carried out with the drug substance ("in vitro biowaiver" [2]).

Therefore, drug permeability screening has become a routine method for the pharmaceutical industry. Many big pharmaceutical companies do these experiments in-house, while others may use one of the numerous specialized contract service labs for such studies.

Standard cell models for drug permeability studies are based on a microwell plate format where cell lines are grown on filter insert supports. The most common cell model of this type is called Caco-2 assay [3], which is frequently used to predict human absorption of the drugs from the intestine. The cells are grown to make a tight barrier of a single layer of cells, a process, which takes approx. 3 weeks during which the cells need frequent attendance in a specialized cell culture lab. For the permeation test, these cell layers on their supports are exposed to the drug solution and the flux of the drug molecules through the cell layer is measured. The assay includes both the passive and the active transport. Numerous specialized labs provide contract service for such studies, if the facilities are not available in-house. The results of such permeation experiments frequently show large variation. An estimation of the very best reproducibility level that can be expected is approx. 50%, as can be estimated from values published by a contractor lab cyprotex [4]. Commonly much more variability is observed. Unfortunately, in addition, the comparability between labs tends to be very poor.

The Franz Cell apparatus [5] is also widely used and the devices needed for the tests are commercially available in different designs. The cell is based on diffusion chambers made of two borosilicate glass component cells.

For the experiments, typically biological tissue is extracted from animals, either kept alive (including active transport) or not (passive transport only), and placed in between the 2 compartments. Flux of drug molecules is measured by collecting samples from the acceptor compartment over time. The handling of this model is laborious and may be unpleasant, and the results are biased by biological variation.

Non-cell based models are the PAMPA (parallel artificial membrane permeability assay) as well as the PVPA (phospholipid vesicle-based permeation assay) model. They are both based on multiwell plates format. The PAMPA model is frequently used for drug screening. It is exclusively commercially available in several variations, with secret composition of both the barrier and the solvents used. In order to make the model robust enough for high throughput, a porous substrate is impregnated with a lipophilic phase to mimic cell membranes. In general, the well plates comprise filter inserts soaked in organic solution of lipids in dodecane, or hexadecane as a lipid compound, or more complex mixtures such as the special tri-layer structures (lipid/oil/lipid). The different PAMPA set-ups and methods of the model vary according to the aim of the study. For the experiment, the membranes need to be freshly soaked with the provided solutions.

The PVPA model (phospholipid vesicle permeation assay) is also a lipid-based model. However, it contains liposomes (closed vesicles of phospholipid bilayers) which resemble cells, in a tight packing. It is believed that this set-up is much more comparable to physiologic properties, and it has shown to predict the passive transport in human oral absorption better than the PAMPA model and as good as the CaCo2-cell assays (passive transport only), with a good reproducibility (about 10% st.dev. for n=3, maximum value 25% [6]).

The method can be automatized for medium throughput; however, the barriers need to be prepared by a laborious procedure, which is not trivial. In brief, liposome dispersions of certain sizes are prepared by extrusion, and deposited on a filter support by centrifugation. The liposomes are added in consecutive steps, starting with the smallest ones. Freeze-thaw cycles are used to tighten the barriers by liposome fusion. The exact procedure is published [6]. The model is used by several research groups, however, it is not commonly used in industry. It has recently been refined to use other lipid compositions and solvents to mimic other biological barriers, e.g. the skin. [7]

PAMPA is commercially available in several variants as complete kits, with long storage time, and it is fast to use. However, the PAMPA barriers are less able to resemble in vivo permeation properties than rather a partitioning into non-physiological oil phases. The barriers show limited resistance to some excipients. The devices only come in the microtiterplate format. The kits are very expensive. PVPA is from a mechanistic point of view based on similar principles of the permeation layer being composed of physiological lipids. However, the experiments are rather laborious to carry out. This is connected to the tedious preparation procedure of the barriers and their lack of long-term stability (they can be frozen and should be used within 2 weeks). The barriers are not commercially available. During an experiment, the barriers cannot be used over a long time due to mechanical reasons, and they are incompatible with many excipients.

The Frantz cell model using tissues needs to standardize the tissues (fresh or frozen). Hence, there is an intrinsic variability according to the origin of the tissue samples. Accessibility of tissues is another serious restriction. Cell-based systems need to be grown in special lab facilities over long time periods (which is a matter of weeks). They include the possibility to study active transport, however, the passive transport is always present and needs to be studied separately. Cell based assays lack reproducibility; the inter-lab variance is so high that data should not be compared even if the same cell line is used. Due to the sensitivity of the cells, they cannot be used with concentrated formulations and some excipients.

Corti et al [8] describe the development of an assay for predicting permeability of drugs across artificial membranes, which is similar to the PAMPA approach. The device used for the assay is a Sartorius absorption simulator model comprising i) a donor compartment for adding a composition comprising the compound, ii) a barrier comprising a porous support phospholipid impregnated with a mixture of phospholipids (<2%), cholesterol and mainly the solvent octanol (96%) on said support, and iii) an acceptor compartment for accepting the compound after permeation of the barrier.

EP1779921A1 discloses an improved phospholipid membrane for use in the PAMPA assay. A porous support made from, e.g. polycarbonate, is initially coated with a non-volatile support liquid, e.g. hexadecane. A phospholipid solution in a volatile solvent is applied to the surface of the porous support and the solvent is allowed to evaporate, leaving a lipid layer on the porous support. The amount of support liquid is preferably minimized (section [0020]) and depending on the amount used, the phospholipid layer may form above the porous support, on the porous support, or within the pores of the support. EP1779921A1 further describes the use of the phospholipids in the PAMPA assay, which is described as a multiplex setup with donor compartments separated from acceptor compartments by way of a barrier comprising the porous support with a phospholipid layer adhering to said support.

The above-mentioned problems have been solved by the present invention by a novel biomimetic artificial barrier for drug permeability studies. The barrier is cost effective and easy to use, and has a much higher chemical resistance in comparison to all other available models. The barriers of the present invention can be adapted to Franz cell diffusion chambers and permeability coefficients of drugs can be measured. Moreover, tightness of the barrier in respect to hydrophilic markers, the resistance of the barriers to proton permeation (pH changes) and shelf-life stability in terms of functionality render them very applicable.

The present invention also seeks to solve the problems associated with prior art barriers when e.g. surfactants and co-solvents are present. Thus it is an objective of the present invention to provide a barrier that can withstand surfactants and co-solvents without affecting the integrity of the barrier and thereby its permeability.

SUMMARY OF THE INVENTION

The present invention is directed to the use of barriers coated with lipids.

Barrier Assembly

In one aspect of the present invention there is provided a barrier assembly (or assay) for predicting permeability of chemical compounds; the barrier assembly comprises:
  a donor compartment for adding a composition comprising the compound;
  a barrier based on a polymeric support and a phospholipid layer adhering to the surface of the polymeric support; and
  an acceptor compartment for accepting the compound upon permeation of the barrier;
wherein the barrier separates the donor and acceptor compartment, and wherein the support comprises 2-4 support sheets sandwiching the phospholipid layers. The polymeric support may be porous or non-porous.

In a further aspect, the invention relates to a barrier assembly for predicting permeability of chemical compounds; the assembly comprises:
  a donor compartment for adding a composition comprising the compound;
  a barrier based on a polymeric support and a phospholipid layer adhering to the surface of the support; and
  an acceptor compartment for accepting the compound upon permeation of the barrier;
said barrier separates the donor and acceptor compartment, said support comprises 2-4 support sheets sandwiching the phospholipid layers, wherein the thickness of the sheets ranges from 0.1-300, preferably 1-150, microns and the thickness of the phospholipid layer ranges from 0.1-300, preferably 1-150, microns.

In another aspect, the invention relates to a barrier assembly (1), for determining permeability of one or more chemical compounds across a biological barrier, the barrier assembly (1) comprising:
  a donor compartment (2) for adding the chemical compound or a composition comprising the compound;
  an acceptor compartment (3) for accepting the compound upon permeation across a barrier (4); and a barrier (4) separating the donor compartment (2) and acceptor compartment (3);

characterized in that said barrier (4) comprises a polymeric support (5), a phospholipid layer (6) adhering to the surface of the polymeric support (5), and a cover layer (7) on top of the phospholipid layer (6).

In the present context, the term "determining permeability" may also be understood as "predicting permeability" since barrier assembly mimics a natural (human) barrier, such as the gastro-intestinal barrier.

FIG. 4 illustrates examples of how a barrier according to the invention may be constructed and FIG. 3 illustrates how a barrier assembly according to the invention may be constructed.

The barrier can be constructed to resemble various biological barriers. One characteristic of biological barriers are their spatial dimensions. In the present invention, the thickness of the barrier can be altered to simulate various barriers, such as cell layers in different tissues made from a variety of lipid compositions.

In an embodiment, the thickness of the polymeric support (5) ranges from 0.1-300 µm, preferably 1-150 µm, even more preferably 2-50 µm. In yet an embodiment the thickness of the phospholipid layer (6) ranges from 0.1-300 µm, preferably 0.5-150 µm, even more preferably 1-20 µm or 4-15 µm.

In another embodiment, the phospholipid layer is present in an amount of 0.05-10 mg/cm$^2$ on the surface of the polymeric support (5), such as 0.1-5 mg/cm$^2$, such as 0.2-3 mg/cm$^2$ or such as 0.4-1 mg/cm$^2$. Thus, it is to be understood that the phospholipid layer forms a layer on top of the polymeric support.

The polymeric support may comprise (or consist of) different materials. Thus, in an embodiment the polymeric support (5) comprises cellulose, cellulose acetate, cellulose nitrate, cellulose hydrate, hydrophilic mixed cellulose esters, polyamides, polyethylene, polypropylene, polyurethane, polyethylenterephthalate, polyvinylfluoride, polyvinylchloride, polyvinylidendifluoride, polytetrafluoroethylen, polysulfones such as hydrophilic polyethersulfone, or polycarbonate, preferably cellulose hydrate. Different materials have been tested by the inventing group. The polymer support is preferably chosen from a material being highly permeable, so that the permeability is primarily being influenced by the phospholipid layer. In the example section, cellulose hydrate has been included as a non-limiting example.

The polymeric support has very small pores compared to other barrier systems. Thus, in an embodiment, the polymeric support (5) comprises pores smaller than 10 nm in diameter, such as smaller than 5 nm in diameter, such as smaller than 2 nm in diameter. In yet an embodiment the diameter of the pores in the polymeric support are in the range 0.05 nm to 10 nm, such as 0.1 nm to 5 nm. Without being bound by theory, it is believed that this small pore size enables the formation of a lipid layer on top of the support instead of a lipid network inside the support layer.

The phospholipid layer may be formed by different phospholipids and other lipids. Thus, in an embodiment the phospholipid layer (6) comprises glycerophospholipids, such as glycerophosphocholines, glycerophosphoethanolamines, glycerophosphoserines, glycerophosphoglycerols, glycerophosphoglycerophosphates, glycerophosphoinositols, glycerophoinositol monophosphates, glycerophosphoinositol bisphosphates, glycerophoinositol trisphosphates, glycerophosphates, glyceropyrophosphates, glycerophosphoglycerophosphoglycerols (cardiolipins), CDP-glycerols, glycerophosphoglucose lipids, glycerophosphoinositolglycans, glycerophosphonocholines, glycerophosphonoethanolamines, di-glycerol tetraether phospholipids (caldarchaeols), glycerol-nonitol tetraether phospholipids, and/or oxidized glycerophospholipids. In another embodiment the phospholipid layer (6) comprises glycerolipids, such as monoacylglycerols, diacylglycerols, triacylglycerols and others, sphingolipids, such as sphingoid bases, ceramides, phosphosphingolipids, phosphonosphingolipids, neutral glycosphingolipids, acidic glycosphingolipids, basic glycosphingolipids, amphoteric glycosphingolipids, arsenosphingolipids and others, sterol lipids, such as sterols, including cholesterol, steroids, secosteroids, such as Vitamin D, derivatives of steroid conjugates, wax esters, fatty acids, triglycerides, squalene, tocopherol, oligopeptides, bile acids and derivatives, hopane, and hopanoids. The lipid compositions may be optimized dependent on the type of barrier the barrier should mimic. In a preferred embodiment, the lipid is egg yolk lecitihine and/or phosphatidylcholine.

In another embodiment, the phospholipid layer (6) further comprises additives, such as hyaluronic acid, carbohydrates, proteins, and their derivatives. In a further embodiment, the additives are selected from the group consisting of surfactants, bile salts, cyclodextrins, lipophilic and hydrophilic polymers. In yet a further embodiment, the phospholipid layer (6) preferably contains less than 15% (w/w), such as less than 10% (w/w), preferably less than 5% (w/w), organic solvent.

In a more specific embodiment, the polymeric support (5) comprises cellulose hydrate and the phospholipid layer (6) comprises phosphatidylcholine.

The inventors have surprisingly found that by adding a cover layer on top of the phospholipid layer, the barrier becomes resistant (retains its integrity) towards surfactants and solvents. Phrased in another way, the polymeric support and the cover layer sandwiches the phospholipid layer. Such resistance is important if the compounds are to be added in a bio-mimicking liquid. The cover layer may be identical to the support layer or different. In an embodiment, the cover layer (7) is selected from the group consisting of cellulose, cellulose acetate, cellulose nitrate, cellulose hydrate, hydrophilic mixed cellulose esters, polyamides, polyethylene, polypropylene, polyurethane, polyethylenterephthalate, polyvinylfluoride, polyvinylchloride, polyvinylidendifluoride, polytetrafluoroethylen, polysulfones such as hydrophilic polyethersulfone, or polycarbonate, preferably cellulose hydrate. The material of the cover layer may be chosen to reflect functional properties in terms of chemical interactions and mechanical stability of biological barriers. Furthermore, the material of the cover layer may be chosen in order to simulate bio-mimetic functions of specific tissues, such as the mucus or epithelium.

In an embodiment, the cover layer is intended do face towards the donor compartment in the barrier assembly. In another embodiment, the cover layer is intended to face towards the acceptor compartment in the barrier assembly. In the case the cover layer is identical to the polymeric support layer, the direction does not matter.

As just described, it is important that the barrier is resistant towards surfactants and solvents. Thus, in an embodiment, the barrier (4) retains its integrity in the presence of surfactants, such as those selected from the group consisting of: non-ionic surfactants such as polysorbates, such as Polysorbat 80 or 60, non-ionic solubilsers and surfactants, such as Cremophor and Triton-X, bile salts, such as taurocholate, cholic acid, lithocholic acid and chenodeoxycholic acid, anionic detergents, such as sodium dodecyl sulfate (SDS) and cationic surface active substances such as cetyl trimethylammonium chloride. Example 3 shows the resistance towards different surfactants and solvents.

In yet an embodiment, the barrier (4) retains its integrity in concentrations of Triton-X of up to 5% (M/M), such as up to 3% or such as up to 1%; and/or SDS up to 10%, such as up to 7% or such as up to 5%; and/or DMSO of up to 15%, such as up to 12% or such as up to 10%; and/or Polysorbate 60 or 80 up to 10%, such as up to 5%; and/or Polyethoxylated castor oil (Cremophor) up to 10%, such as up to 5%; and/or ethanol up to 10%, such as up to 7% or such as up to 4%.

It is to be understood that the barrier may also retains its integrity at even higher concentrations.

The barrier is also be resistant towards bio-mimetic media (BMM). Thus, in an embodiment, the barrier (4) retains its integrity in solutions of bio-mimetic media (BMM), such as FaSSIF, FaSSIF-V2, FeSSIF or FeSSIF-5 V2. In Example 4 and 5, the integrity of the barrier assembly according to the invention was tested in different solutions of bio-mimetic media (BMM).

The barrier should also stable (resistant) at different pHs. Thus, in an embodiment the barrier retains its integrity at a pH range of 1-9, such as 2-9, such as 4-9 or such as 5-8. FIG. 8 illustrates the pH stability of the barrier according to the invention.

In the present context the term "resistant towards" and "retains its integrity" is to be understood as the barrier has a substantially unchanged permeability to test compounds when compared to a PBS buffer (see table 1 in example 3). Substantially unchanged may be understood as the permeability of tested compounds is not increased by more than a factor 5 when compared to test in PBS, such as not more than a factor 4, such as not more than a factor 3, such as not more than a factor 2. Such permeation may be determined as described for the numbers in table 1.

As illustrated in FIG. 4, it is envisioned that the barrier may comprise several alternating layers of polymeric support (5) and phospholipid layer (6), and a cover layer (7). In the present context, the term "alternating layers" means a first polymeric support followed by a first phospholipid layer followed by a second polymeric support followed by a second phospholipid layer and so on. Thus, in yet an embodiment, the barrier (4) comprises two or more alternating layers of polymeric support (5) and phospholipid layer (6), and a cover layer (7), such as three or more alternating layers of polymeric support (5) and phospholipid (6), and (finished by) a cover layer (7), such as 1-5 alternating layers of polymeric support (5) and phospholipid (6), and (finished by) a cover layer (7), such as 1-4, such as 2-4, such as 2-3 alternating layers of polymeric support (5) and phospholipid (6), and (finished by) a cover layer (7). As mentioned above, the cover layer may be identical to the polymeric support (5).

In an embodiment, the donor compartment (2) or the acceptor compartment (3) or both compartments (2 and 3) are loaded with a liquid composition comprising polysorbate, such as Polysorbat 80 or 60, bile salts, such as taurocholate, cholic acid, lithocholic acid and chenodeoxycholic acid; and/or non-ionic solubilisers and surfactants, such as Cremophor and Triton-X; and/or anionic detergents, such as sodium dodecyl sulfate (SDS); and/or cationic detergents; and/or Bio-mimetic media (BMM) solutions, such as FaSSIF, FaSSIF-V2, FeSSIF or FeSSIF-5 V2; and/or one or more organic solvents.

As mentioned above the barrier is resistant towards such compositions.

In a further embodiment, the donor compartment (2) is provided with a fill port opening to permit the introduction of a compound and a vehicle into the donor compartment (2) and the acceptor chamber (3) is provided with a sampling port.

It may be advantageous if the barrier assembly could readily be inserted in a measuring device. Thus, in an embodiment the barrier assembly (1) is adapted to fit into a measuring cell of a chemical analysis instrument, such as a UV/VIS spectrophotometer, mass spectrometer, NMR spectrometer or fluorimeter.

As mentioned above, the barrier may mimic different (human) biological barriers. Thus, in an embodiment the biological barrier is selected from the group consisting of (human) gastro-intestinal barrier, the (human) blood brain barrier (BBB), nasal, buccal, dermal, rectal, vaginal, ocular, pulmonal, skin, cornea or vesicular barriers.

The type of compound or composition, which may be tested in the assembly according to the present invention, may vary. Thus, in a further embodiment, the one or more chemical compounds are selected from the group consisting of drug substances, drug candidates, medical preparations, drug formulations, drugs, food/feed ingredients, and food/feed compositions, other chemical compounds such as (environmental) toxins or bacterial toxins.

The present inventors have found that the function of the barrier assembly of the present invention is in particular unaffected by the presence of protons (pH changes, see FIG. 6) and has a prolonged shelf-life stability in terms of functionality. The barrier assembly constitutes a viable tool for fast, cost effective, and reliable screening of passive permeability of drugs and chemical entities. Moreover, the barrier can withstand different surfactants and co-solvents without affecting the integrity of the barrier and thereby its permeability to chemical compounds.

The support may comprise one or more sheets of cellulose, cellulose acetate, cellulose nitrate, cellulose hydrate, hydrophilic mixed cellulose esters, polyamides, polyethylene, polypropylene, polyurethane, polyethylenterephthalate, polyvinylfluoride, polyvinylchloride, polyvinylidendifluoride, polytetrafluoroethylen, polysulfones, such as hydrophilic polyethersulfone, or polycarbonate, or composites thereof.

In a preferred embodiment of the present invention the phospholipid layer comprises glycerophospholipids, such as glycerophosphocholines, glycerophosphoetanolamines, glycerophosphoserines, glycerophosphoglycerols, glycerophosphoglycerophosphates, glycerophosphoinositols, glycerophosphoinositol monophosphates, glycerophosphoinositol bisphosphates, glycerophosphoinositol trisphosphates, glycerophosphates, glyceropyrophosphates, glycerophosphoglycerophosphoglycerols (cardiolipins), CDP-glycerols, glycerophosphoglucose lipids, glycerophosphoinositolglycans, glycerophosphonocholines, glycerophosphonoethanolamines, di-glycerol tetraether phospholipids (caldarchaeols), glycerol-nonitol tetraether phospholipids, and/or oxidized glycerophospholipids.

In a particularly preferred embodiment, the support comprises 2-4 support sheets sandwiching phospholipid layers.

The barrier assembly may be adapted to fit into a measuring cell of a chemical analysis instrument, such as a spectrophotometer.

In an embodiment, the donor compartment is provided with a fill port opening into the donor compartment to permit the donor compartment to have a compound and a vehicle introduced into the donor compartment.

The phospholipid layer may further comprise glycerolipids (such as monoradylglicerols, diradylglycerols, triradylglicerols and others), sphingolipids (sphingoid bases, ceramides, phosphosphingolipids, phosphonosphingolipids, neutral glycosphingolipids, acidic glycosphingolipids, basic glycosphingolipids, amphoteric glycosphingolipids, arsenosphingolipids and others), sterol lipids (such as sterols (for example cholesterol), steroids, secosteroids, such as Vitamin D, derivatives of steroid conjugates, wax esters, fatty acids, triglycerides, squalene, tocopherol, oligopeptides, bile acids and derivatives, hopane, and hopanoids.

The phospholipid layer may further comprise additives, such as hyaluronic acid, carbohydrates, proteins, and their derivatives (e.g. glycosylated proteins).

Preferably, the additives are selected from the group consisting of surfactants, bile salts, cyclodextrins, lipophilic and hydrophilic polymers.

Barrier

In a further aspect the invention relates to a barrier (4), for determining permeability of one or more chemical compounds across a biological barrier, characterized in that said barrier (4) comprises a polymeric support (5), a phospholipid layer (6) adhering to the surface of the polymeric support (5), and a cover layer (7) on top of the phospholipid layer (6).

Schematic illustrations of a barrier according to the present invention is given in FIGS. 4A and 4B.

It is to be understood that the embodiments disclosed for the barrier in connection with the barrier assembly, also is combinable with the aspect relating to the barrier in its own right. The same is to be understood for all aspects of the invention.

Use of Barrier Assembly

The barrier assembly and barrier according to the present invention may be used in different ways. Thus, another aspect of the invention relates to the use of a barrier assembly (1) according to the present invention or a barrier (4) according to the present invention, for determining permeability of one or more chemical compounds across a biological barrier.

In an embodiment, said one or more chemical compounds are added in a solution of BMM. In a further embodiment, the biological barrier is selected from the group consisting of (human) gastro-intestinal barrier, the (human) blood brain barrier (BBB), nasal, buccal, dermal, rectal, vaginal, ocular, pulmonal, skin, cornea or vesicular barriers.

Method of Use

In yet another aspect, the invention relates to a method for determining the permeability of one or more compounds across a biological barrier, the method comprising
providing a barrier assembly (1) according to the invention;
adding a compound or composition comprising the compound to the donor compartment (2) of the barrier assembly (1); and
measuring the amount of the compound permeating into the acceptor compartment (3).

In an embodiment the method further comprising determining the permeability of the compound.

In a further embodiment the donor compartment (2) is loaded with a liquid composition comprising
polysorbate, such as Polysorbat 80 or 60, bile salts, such as taurocholate, cholic acid, lithocholic acid and chenodeoxycholic acid; and/or
non-ionic solubilisers and surfactants, such as Cremophor and Triton-X; and/or
anionic detergents, such as sodium dodecyl sulfate (SDS); and/or cationic detergents, and/or
Bio-mimetic media (BMM) solutions, such as FaSSIF, FaSSIF-V2, FeSSIF or FeSSIF-5 V2; and/or
one or more organic solvents.

Process for Preparing Barrier

The present invention also provides process for preparing a barrier based on a polymeric support and a phospholipid layer adhering to the polymeric support comprising the steps of 1) optionally mixing a phospholipid component and a volatile solvent, such as water, methanol, ethanol, propanol, isopropanol, chloroform, acetone, t-butanol, ethylacetate, diethylether, methylenchlorid, trichlorethan, trichlorethen, tetrahydrofuran; or mixtures thereof
2) applying the phospholipid component onto the surface of the support in order to establish a phospholipid layer, said support comprises 2-4 support sheets sandwiching the phospholipid layers; and
3) drying the phospholipid component. The thickness of the sheets ranges from 0.1-300, preferably 1-150, microns and the thickness of the phospholipid layer ranges from 0.1-300, preferably 1-150, microns.

In yet a further aspect the invention relates to a process for preparing a barrier (4) comprising a polymeric support (5), a phospholipid layer (6) adhering to surface of the polymeric support (5), and a cover layer (7) on top of the phospholipid layer (6), comprising the steps of:

1) optionally, mixing a phospholipid component and a volatile solvent, such as water, methanol, ethanol, propanol, isopropanol, chloroform, acetone, t-butanol, ethylacetate, diethylether, methylenchlorid, trichlorethan, trichlorethen, tetrahydrofuran;
2) applying the phospholipid component onto the surface of a first polymeric support in order to establish a first phospholipid layer adhering to the first polymeric support;
3) drying the phospholipid component;
4) optionally repeating steps 2) and 3) to add one or more alternating secondary layers of alternative phospholipid composition
5) optionally, repeating step 1) to 3) to add two or more alternating secondary layers of polymeric support and phospholipid to the first phospholipid layer; and
6) applying a cover layer on top of the first or secondary phospholipid layer.

In an embodiment, the thickness of the polymeric support (5) ranges from 0.1-300 µm, preferably 1-150 µm, even more preferably 2-50 µm. In yet an embodiment, the thickness of the phospholipid layer (6) ranges from 0.1-300 µm, preferably 0.5-150 µm, even more preferably 1-20 µm.

In another embodiment, the phospholipid layer (6) comprises glycerolipids, such as monoacylglycerols, diacylglycerols, triacylglycerols and others, sphingolipids, such as sphingoid bases, ceramides, phosphosphingolipids, phosphonosphingolipids, neutral glycosphingolipids, acidic glycosphingolipids, basic glycosphingolipids, amphoteric glycosphingolipids, arsenosphingolipids and others, sterol lipids, such as sterols, including cholesterol, steroids, secosteroids, such as Vitamin D, derivatives of steroid conjugates, wax esters, fatty acids, triglycerides, squalene, tocopherol, oligopeptides, bile acids and derivatives, hopane, and hopanoids.

In yet another embodiment the polymeric support (5) comprises cellulose, cellulose acetate, cellulose nitrate, cellulose hydrate, hydrophilic mixed cellulose esters, polyamides, polyethylene, polypropylene, polyurethane, polyethylenterephthalate, polyvinylfluoride, polyvinylchloride, polyvinylidendifluoride, polytetrafluoroethylen, polysulfones as hydrophilic polyethersulfone, or polycarbonate.

In yet a further embodiment the phospholipid layer (6) further comprises additives, such as hyaluronic acid, carbohydrates, proteins, and their derivatives.

In an embodiment, the additives are selected from the group consisting of surfactants, bile salts, cyclodextrins, lipophilic and hydrophilic polymers.

In another embodiment, the phospholipid layer (6) has been applied onto the polymeric support (5) by spraying, molding, casting, or solid layering.

In an embodiment the thickness of the sheets ranges from 0.1-300, preferably 1450, microns and the thickness of the phospholipid layer ranges from 0.1-300, preferably 1-150, microns.

In yet an embodiment, the phospholipid layer comprises glycerolipids, such as monoradylglicerols, diradylglycerols, triradylglicerols and others, sphingolipids, such as sphingoid bases, ceramides, phosphosphingolipids, phosphonosphingolipids, neutral glycosphingolipids, acidic glycosphingolipids, basic glycosphingolipids, amphoteric glycosphingolipids, arsenosphingolipids and others, sterol lipids, such as sterols, including cholesterol, steroids, secosteroids, such as Vitamin D, derivatives of steroid conjugates, wax esters, fatty acids, triglycerides, squalene, tocopherol, oligopeptides, bile acids and derivatives, hopane, and hopanoids.

In yet a further embodiment, the support comprises sheets of cellulose, cellulose acetate, cellulose nitrate, cellulose hydrate, hydrophilic mixed cellulose esters, polyamides, polyethylene, polypropylene, polyurethane, polyethylenterephthalate, polyvinylfluoride, polyvinylchloride, polyvinylidendifluoride, polytetrafluoroethylen, polysulfones as hydrophilic polyethersulfone, or polycarbonate.

In another embodiment, the phospholipid layer further comprises additives, such as hyaluronic acid, carbohydrates, proteins, and their derivatives. In an embodiment, the additives are selected from the group consisting of surfactants, bile salts, cyclodextrins, lipophilic and hydrophilic polymers.

In a further embodiment, the phospholipid layer has been applied onto the support by spraying, molding, casting, or solid layering.

The phospholipid component adhering to the support preferably contains less than 15% (w/w), such as less than 10%, (w/w), preferably less than 5% (w/w), organic solvent. In this way, a more reliable flux mimicking a biological membrane is achieved.

In yet an embodiment, the process further comprises incorporating the barrier in a barrier assembly comprising
 a donor compartment (2) for adding the chemical compound or a composition comprising the compound;
 an acceptor compartment (3) for accepting the compound upon permeation of a barrier (4); and
wherein the incorporated barrier (4) separates the donor compartment (2) and acceptor compartment (3). It is to be understood that the barrier assembly may be for predicting permeability of one or more chemical compounds across the (human) gastro-intestinal barrier.

In sum, the biomimetic barrier of the present invention is compatible with a wide range of surfactants/co-solvents including Polysorbate 80, DMSO in rather high concentrations, even Triton-X at 1%. Also, the barrier of the present invention copes with different bio-mimetic media, such as FaSSIF, FaSSIF-V2, FeSSIF and FeSSIF-V2. Accordingly, the present inventors have provided a fast and reliable prediction of passive drug permeability.

Barrier Obtained/Obtainable by Process

A further aspect of the invention relates to a barrier obtainable/obtained by a process according to the invention.

In another aspect, the invention relates to a barrier based on a support and a phospholipid layer adhering to the support obtainable by the process according to the invention.

An aspect relates to the barrier assembly (1) according to the invention, wherein the barrier (4) is obtainable/obtained by a process according to the invention.

Another aspect relates to a barrier (4) based on a polymeric support (5), a phospholipid layer (6) adhering to the polymeric support (5), and a cover layer (7) on top of the phospholipid layer (6) obtainable by the process according to the invention.

DETAILED DESCRIPTION OF THE INVENTION

Figure 1:
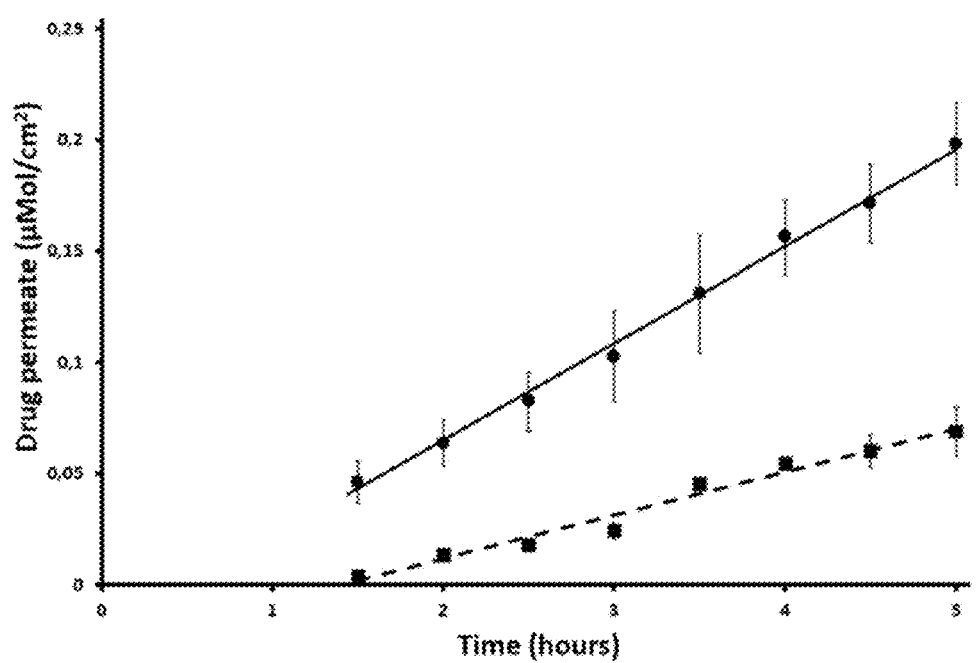
FIG. 1 shows a comparison of fluxes of calcein and hydrocortisone through the barrier of the present invention.

Cheap and straightforward production processes that are well known and frequently used in large-scale production for mass products can be used to produce the barriers and permeation devices. The set-up is flexible and is easy to change according to special needs. The barrier layers can be modified according to specific needs as well in terms of properties and composition both of the supports (foil; "membrane") as well as the coating materials (e.g. lipids and excipients).

The technical format of the barrier inserts (and complete devices; kits) can be modified according to experimental set-up preferred, e.g. Frantz cell. There are practically no restrictions in size (diameter) and shape (round, elongated etc). The barriers or even complete devices can be pre-produced in large scale and stored for comparably long time, which makes it possible to ship both the barriers or complete devices.

The barriers of the present invention are mechanically more stable and more resistant against excipients than any other of the models. This enables alternative experimental methods to be used. For such permeation experiments only standard lab equipment is needed. There is practically no waiting time (compared to growing of cells for 3 weeks). The reproducibility is good; there is no additional inter-lab variance. The present invention utilizes physiologic lipids in a production process, which is time- and cost effective, and the product is flexible in format, easy to use, and can be adjusted to mimic various biological barriers.

Moreover, the present invention envisages different lipid/excipient compositions, technical procedures of applying the coat (by spraying, molding, casting, solid powder layering etc.), layer thicknesses and adjustment of other processing parameters (e.g. addition of moisture, solvents, drying conditions, temperature treatment). These features could of course further strengthen the patentability if some unexpected benefit is achieved thereby.

The aim of the present invention is to provide a new flexible and cheaper permeation model that is straightforward to produce, easier to handle and predictive for several passive transport ways.

The first part of the invention is the composition and manufacture of the barriers. In this respect standard commercially available foils, such as cellulose, cellophane or cellulose hydrate membranes (e.g. dialysis tubing) are used as a support which is coated (layered) with a dispersion of excipients and lipids, preferably including physiological lipids. The specific composition of such coat can be varied to mimic certain cell lipid membranes and barriers, e.g. to mimic blood brain barrier, transdermal delivery, ocular delivery etc.

According to the drug transport path of interest, the entire barrier may comprise several layers of foils and dispersions. The overall tightness of the barrier in terms of specific permeation and of permeation rate can be adjusted by common processing and manufacturing adjustments, such as different lipid/excipient compositions, technical procedures of applying the coat (by spraying, molding, casting, solid powder layering etc.), layer thicknesses and adjustment of other processing parameters (e.g. addition of moisture, solvents, drying conditions, temperature treatment).

It is an additional advantage that the technology implemented with the present invention is not limited to a special test format or any of those available on the market; it can not only be used in commercially available Frantz cells or well plates, but also in other devices, that may even circumvent the current restrictions in maximum diameter of the permeation barriers, because the barriers are mechanically more stable. Since the barriers of the present invention can be produced in almost any size, experimental set-ups can be tailored to special needs, e.g. for automation and in-line measurements.

Furthermore, the barriers are comparably resistant to chemicals, which means that certain formulations and more concentrated donor or acceptor phases can be tested as well. The second part of the invention is the design of new formats for entire devices (including holders and compartments for donor and acceptor) which are preferably made from glass, metal, or plastic material. New designs can easily be developed for special needs. This opens up for the possibility to adjust e.g. volumes and properties of the studied solutions, use of concentrated formulations and excipients, or to simplify handling.

The production processes for both the barriers as well as complete devices are flexible and straightforward based on available technologies.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

Permeability of a hydrophilic marker compound (calcein) and a drug compound (hydrocortisone) is measured through a barrier according to the present invention.

A sheet of cellulose hydrate was prewashed in demineralized water. The sheet was put on a flat surface and sprayed with a 1% (M/M) solution of egg yolk lecithin (E-80, Lipoid GmbH, Ludwigshafen, Germany) in ethanol. The total amount of phospholipids deposited was 0.4 to 0.5 mg/cm$^2$. Once the organic solvent was evaporated, two coated sheets were placed one upon the other, sandwiching the phospholipids.

Frantz cells with a permeation surface of 1 cm$^2$, a maximum volume in the upper compartment of 1.8 mL and a fixed volume in the bottom compartment of 8 mL were used.

The barrier was placed in between of the donor and the acceptor chamber, and a permeation experiment was performed at 25° C.

A saturated dispersion of hydrocortisone in phosphate buffer (pH 7.4) was placed in the 8 mL lower compartment. The barrier was placed in between the lower and upper compartment and at time zero (start of the experiment), 1.8 mL of phosphate buffer solution (pH 7.4) was placed into the upper compartment. Every 30 minutes, 0.2 mL of the solution in the upper compartment were withdrawn and drug concentration quantified by HPLC. The removed volume was replaced with an equal volume of fresh buffer.

8 mL of phosphate buffer solution was placed into the lower compartment. The barrier was placed, and at time zero (start of the experiment) 1.5 mL of a 10 mM phosphate buffer solution of calcein was placed in the upper compartment. Every 60 minutes, 0.2 mL of the solution in the lower compartment were withdrawn and calcein concentration quantified by fluorescence spectroscopy. The removed volume was replaced with an equivalent amount of fresh buffer.

FIG. 1 shows the comparison between the amounts of hydrocortisone and calcein permeating through the barrier over the time and surface. The permeability coefficient (P) calculated for hydrocortisone was $1.27 \pm 0.15 \ast 10^{-5}$ cm/sec whereas for calcein was $0.12 \pm 0.01 \; 10^{-5}$ cm/sec cm/sec, indicating that hydrocortisone is better permeable through the barrier in comparison to calcein.

Example 2

In this example, the permeabilities of three drugs were compared with the permeability of the marker compound calcein through the barrier described in Example 1. Similar results have been obtained using S100.

Figure 2:
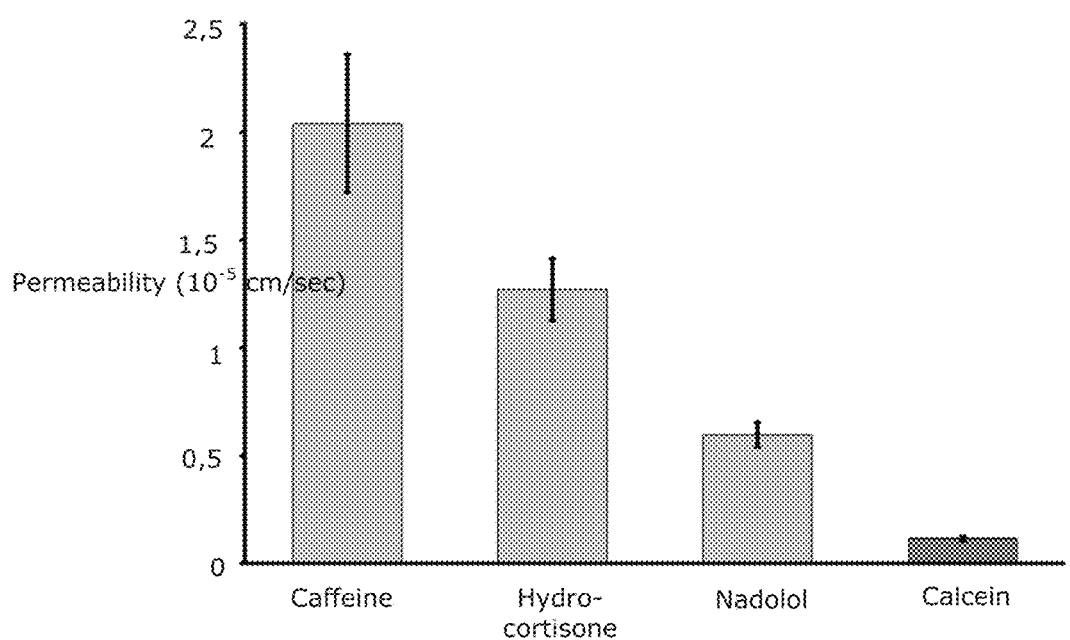
FIG. 2 shows the permeabilities of hydrocortisone, nadolol, and caffeine compared with the marker calcein through the barrier of the present invention.
Figure 3:
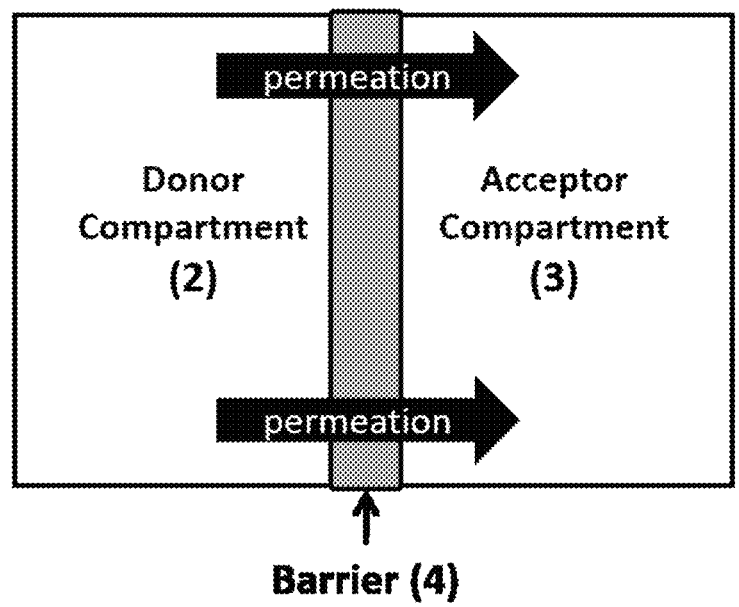
FIG. 3 shows the set up for a permeability experiment comprising of a donor, compartment (2), the barrier of the present invention (4) and an acceptor compartment (4).
Figure 4:
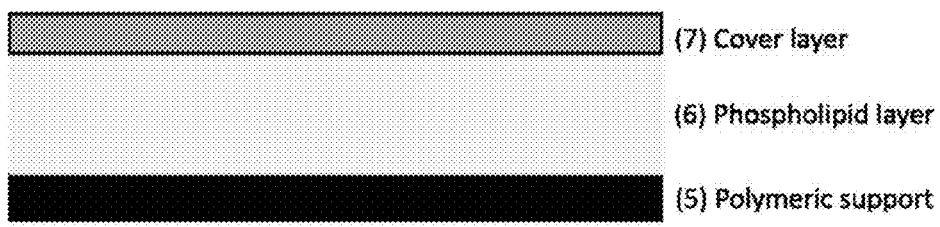
FIG. 4 shows the general composition and structure of the barrier of the present invention. The barrier comprises a polymeric support (5), a phospholipid layer (6) adhering to the surface of the polymeric support (5), and a cover layer (7) on top of the phospholipid layer (6) (A). The barrier may comprise further layers (B).
Figure 4:

FIG. 2 shows the permeability coefficients of hydrocortisone, nadolol, and caffeine compared with the marker calcein through the barrier of the present invention. These data are in agreement with permeabilities measured in other assays and indeed mimic the corresponding fluxes over biological membranes.

Since the three compounds cover a representative selection for such assays it is concluded that the barrier of the present invention is very applicable for such measurements.

Example 3

According to the present example, the permeability of a hydrophilic marker compound (calcein) and a drug compound (hydrocortisone) is measured through a barrier according to the present invention. The integrity of the barrier was measured only by calcein permeability studies as suggested by (Flaten, Dhanikula et al. 2006 [9]).

The aim of this example is to evaluate how surfactants, co-solvents would affect the barrier of the present invention.

Permeability studies were carried out employing surfactants and co-solvents as media, along with the hydrophilic marker calcein, which is used in high concentration to show possible leaks of the barrier. The apparent permeability coefficients ($P_{app}$) were determined and compared to the values in buffer, and to literature on other in-vitro models.

For all permeability studies, Franz diffusion cells with a surface area of 1 cm$^2$, upper chamber nominal volume of 2 mL and lower chamber volume of 8 mL were employed. The donor phase (upper chamber) was filled with 1.5 mL hydrophilic marker calcein (5 mM) and different surfactants and solvents, whereas the acceptor compartment (lower chamber) was filled with 8 mL PBS (7.4±0.05). The barrier was placed between the donor and acceptor compartment and the flux (3) of calcein was measured over time. The permeability studies were carried out over a 5 hours period, and samples of 200 µL were withdrawn from the acceptor chamber every 30 min for the first 2 hours and then every 60 min. The withdrawn sample volume was replaced with an equal amount of fresh PBS at each time point. The samples were analyzed by fluorescence spectroscopy employing a BMG Fluostar Omega 96 plate reader (wavelength of excitation 485-512 nm and emission 520 nm, BMG Labthech GmbH, Ortemberg, Germany).

Table 1 shows the permeability of calcein through the barrier in the presence and absence of surfactants and co-solvents. It is visible that the permeation of calcein through the empty barrier support is much faster. Specifically, the permeability of calcein is approx. 10 times higher as compared to the barrier of the present invention. This result is expected, since it has been proven that the lipid layer contained in the barrier has a significant retention on the permeability of hydrophilic compounds.

TABLE 1

Permeability coefficient ($P_{app}$) for calcein in the presence of the different surfactants and co-solvents in the donor chamber, or media in the acceptor chamber respectively, compared to the $P_{app}$ of calcein in PBS and barrier support.

|  |  | Concentration (%) | Permeability ($P_{app}$) ($10^{-5}$ cm/s) |
|---|---|---|---|
|  | Barrier support[i] | — | 1.65 (0.10) |
|  | PBS[i] | — | 0.12 (0.01) |
| Surfactants and co-solvents | Triton-X | 1 | 0.12 |
|  | Ethanol | 4 | 0.12 |
|  | Tween 60 ® | 4 | 0.15 |
|  | Tween 80 ® | 5 | 0.06 |

TABLE 1-continued

Permeability coefficient ($P_{app}$) for calcein in the presence of the different surfactants and co-solvents in the donor chamber, or media in the acceptor chamber respectively, compared to the $P_{app}$ of calcein in PBS and barrier support.

|  | Concentration (%) | Permeability ($P_{app}$) ($10^{-5}$ cm/s) |
|---|---|---|
| *Cremophor ® | 5 | 0.12 (0.01) |
| SDS | 5 | 0.21 |
| DMSO | 10 | 0.15 |

[i]Standard deviation is shown in the parentheses for mean permeability values (n = 3-5).
*Permeability study was carried out in the Ussing chambers Results obtained with of the present invention shows that both "PBS" and the empty "barrier support" have shown low Standard Deviations (SD), respectively 8% and 6% SD. Since the SD is so low, even small changes in permeability would be considered significantly different. Therefor even though the permeability of calcein is in some cases increased, the permeability can still be considered very low when comparing the permeability of calcein in the presence of surfactants, to the "barrier support" (1.65±0.1·$10^{-5}$ cm/s). Results from Table 1 clearly indicate that none of the surfactants in the given concentrations affects the permeability of calcein enough to imply that the retention properties of the barrier has been compromised.

The permeability of calcein through Permpeapad™ (barrier of the invention) with 4% EtOH and 10% DMSO were 0.12·$10^{-5}$ cm/s and 0.15·$10^{-5}$ cm/s—these results were not significantly different and thus compatible with the barrier of the present invention.

Both PVPA and PVPA$_{biomimetic}$[10] have shown not to be compatible with Cremophor®. The permeability of calcein, through the current barrier with 5% Cremophor® was 0.23·$10^{-5}$ cm/s. That is approximately a 2-fold increase, which was considered significantly different (p<0.05) and thus more explorative barrier stability experiments were carried out. Since the solutions appear to be more viscous than PBS, Ussing chambers were used due to better stirring. Preliminary studies have shown that the permeability of drugs, on Franz cell and side-by-side diffusion chamber can be compared directly when taking initial concentration ($C_0$) and surface area (A) into consideration (data not shown). Results obtained for the permeability of calcein through the barrier of the present invention with 5% cremophor in the Ussing chambers was 0.12±0.01·$10^{-5}$ cm/s, which is the same as in "PBS". This concludes that Cremophor® up to 5% does not affect the present invention.

Both PVPA and PVPA$_{biomimetic}$[10] were not compatible with Polysorbat 80 in low concentrations. In both cases, the permeability of calcein was significantly increased, due to Polysorbat 80's destructive effect on the lipid barriers. However, for the barrier of the present invention permeability was not increased, but decreased. This also indicates that Polysorbat 80 does not disrupt the barrier, but instead may interact with calcein.

The most interesting observation made was with Triton-X, which is often used in cell-based in-vitro models as a positive control in a concentration range of 0.1-0.5%, destroying the barrier for recovery measurement. Studies with PVPA$_{biomimetic}$ (Naderkhani, Isaksson et al. 2014 [10]) have used Triton-X in a concentration of 0.05%, as a positive control—showing that PVPA$_{biomimetic}$ lost its integrity. Results obtained here show that 20 fold Triton-X concentration (up to 1%) did not affect the integrity of the barrier. The permeability of calcein through the barrier was unchanged when comparing the "PBS" with the presence of Triton-X: both resulted in $0.12 \cdot 10^{-5}$ cm/s.

Results clearly show that the barrier of the present invention can withstand the different surfactants, co-solvents and Triton-X listed in FIG. 1 without affecting the functional integrity of the barrier and thereby the permeability of calcein.

Example 4

FaSSIF and FeSSIF are interesting to use as solvents on the donor side, since they mimic the gastrointestinal fluids in both the fed and fasted state. Using the BMM in in-vitro studies may therefore give a more representative indication of how the drug might behave in-vivo.

Bio-mimetic Media (BMM) solutions, namely FaSSIF, FaSSIF-V2, FeSSIF and FeSSIF-V2 (Biorelevant Inc. London, UK) were prepared according to information provided by the manufacturer. FaSSIF solution were stored for 2 hours prior to use (equilibration time) whereas FaSSIF-V2 and FeSSIF-V2 were stored for 1 h prior to use.

Permeability studies with the different BMM's were carried out on two different permeability setups; FaSSIF and FaSSIF-V2 were employed on the Franz cell permeability setup. FeSSIF and FeSSIF-V2 were carried out on the side-by-side diffusion chamber, due to difficulties when employed on the Franz cell connected to higher viscosity. When FeSSIF and FeSSIF-V2 were employed on the Franz cell setup, some complications occurred. Calcein was layered on the top of the acceptor compartment not mixing properly with the rest of the acceptor media. Even though there was magnetic stirring in the acceptor chamber, the magnet was too small to mix the media properly. This behavior is connected to the composition of FeSSIF and FeSSIF-V2, since both contain substantial amounts of sodium taurocholate (NaTC) and lecithin there is bound to be an increased viscosity of the media. FeSSIF and FeSSIF-V2 were therefore employed on the side-by-side diffusion chamber where the magnetic stirring was more vigorous—resulting in an even distribution of calcein in the respective cells.

The BMM were used as acceptor media in order to determine if they would affect the integrity of the barrier. They were not employed as donor media, since a micellar interaction with calcein and the excipients of the BMM might occur. This might in consequence affect the permeability of calcein, and it would not be possible to know if the changes in permeability were due to the micellar interaction or the BMM's effect on the barrier. The barrier of the present example does not distinguish between donor and acceptor side, and the acceptor side was chosen for the BMM. The results obtained from the permeability setups are presented in Table 2. The results show that the permeability values for calcein employing FaSSIF ($0.21\pm0.03 \cdot 10^{-5}$ cm/s), FaSSIF-V2 ($0.17\pm0.03 \cdot 10^{-5}$ cm/s) and FeSSIF-V2 ($0.23\pm0.05 \cdot 10^{-5}$ cm/s) as acceptor media resulted in slightly increased permeability values. Despite the slightly increased permeability values, the barrier of the present invention was still considered low, when compared to the "Barrier support".

TABLE 2

Permeability coefficient (Papp) for calcein in PBS and through the barrier support compared to Papp of calcein with biomimetic media in the acceptor chamber.

|  |  | Concentration (%) | Permeability (Papp) ($10^{-5}$ cm/s) |
|---|---|---|---|
|  | Barrier support | — | 1.65 (0.10) |
|  | PBS | — | 0.12 (0.01) |
| Media | FaSSIF | — | 0.21 (0.03) |
|  | FaSSIF-V2 | — | 0.17 (0.03) |
|  | FeSSIF$^i$ | — | 0.53 (0.09) |
|  | FeSSIF-V2$^i$ | — | 0.23 (0.05) |

(n = 3-6) Standard deviation is shown in the parentheses
$^i$Permeability studies carried out in Using chamber, due to increased viscosity ref. for compositon of FaSSIF and FESSIF: Jantratid, E., N. Janssen, C. Reppas and J. B. Dressman (2008). "Dissolution media simulating conditions in the proximal human gastrointestinal tract: An update." *Pharmaceutical Research* 25(7): 1663-1676.

However, FeSSIF ($0.53\pm0.09 \cdot 10^{-5}$ cm/s) showed to increase permeability of calcein significantly, and thus more explorative barrier functionality stability experiments were carried out. The results obtained from the explorative barrier functionality studies showed that FeSSIF does not affect the barrier itself: after having a 5 hour exposure to FeSSIF and consecutive rinsing, the very same barrier showed a P$_{app}$ for calcein in PBS of $0.27\pm0.05 \cdot 10^{-5}$ cm/s. If FeSSIF should in some way compromise the barrier, the permeability of calcein would be expected to be as high as in the FeSSIF experiment carried out before ($0.53\pm0.09 \cdot 10^{-5}$ cm/s) and this is not the case. It is quite clear that it is the FeSSIF itself that increases the permeability of calcein. A possible reason might be the high osmolality of FeSSIF ($635\pm10$ mosm) which creates an osmotic pressure difference to the isotonic donor ($285\pm5$ mosm). The osmotic pressure difference might lead to an increase in permeability.

Example 5

Since we could not understand these data for calcein, further permeability experiments with FeSSIF as acceptor media were carried out with caffeine as a model drug. Results showed that the permeability of caffeine though the barrier was unchanged, regardless of the media used in the acceptor chamber. A t-test showed no significant difference (P>0.05). This indicated that the presence of FeSSIF does not affect the barrier of the present invention nor results in loos of integrity.

The effect of FaSSIF on Caco-2 cells has previously been investigated by (Ingels, Beck et al. 2004, Fossati, Dechaume et al. 2008 [12]). Results concluded that FaSSIF was compatible with Caco-2 cells and could improve the physiological relevance of them.

The PVPA model was also investigated in relation to FaSSIF compatibility (Fischer, Buckley et al. 2012 [11]). Results showed PUPA to be compatible with FaSSIF—an increase in SD was observed, but the PVPA barriers remained intact. There are no recent studies showing PVPA's compatibility with FaSSIF-V2 and FeSSIF-V2. The present barrier showed good resistance towards all four BMMs.

The (mixed) micelles that NaTC/Lecithin might form is relevant for passive diffusion of drugs, since it mimics the physiological conditions, and thereby comes more closely to a better IVIVC—this is relevant for all in-vitro models and barrier of the present invention.

Example 6

To verify the influence that different lipid composition might have on the biomimetic properties of the barrier described in the present invention, permeability of a series of drug was tested through barriers manufactured with different lipids (egg yolk lecithin or phosphatidylcholine).

Figure 5:
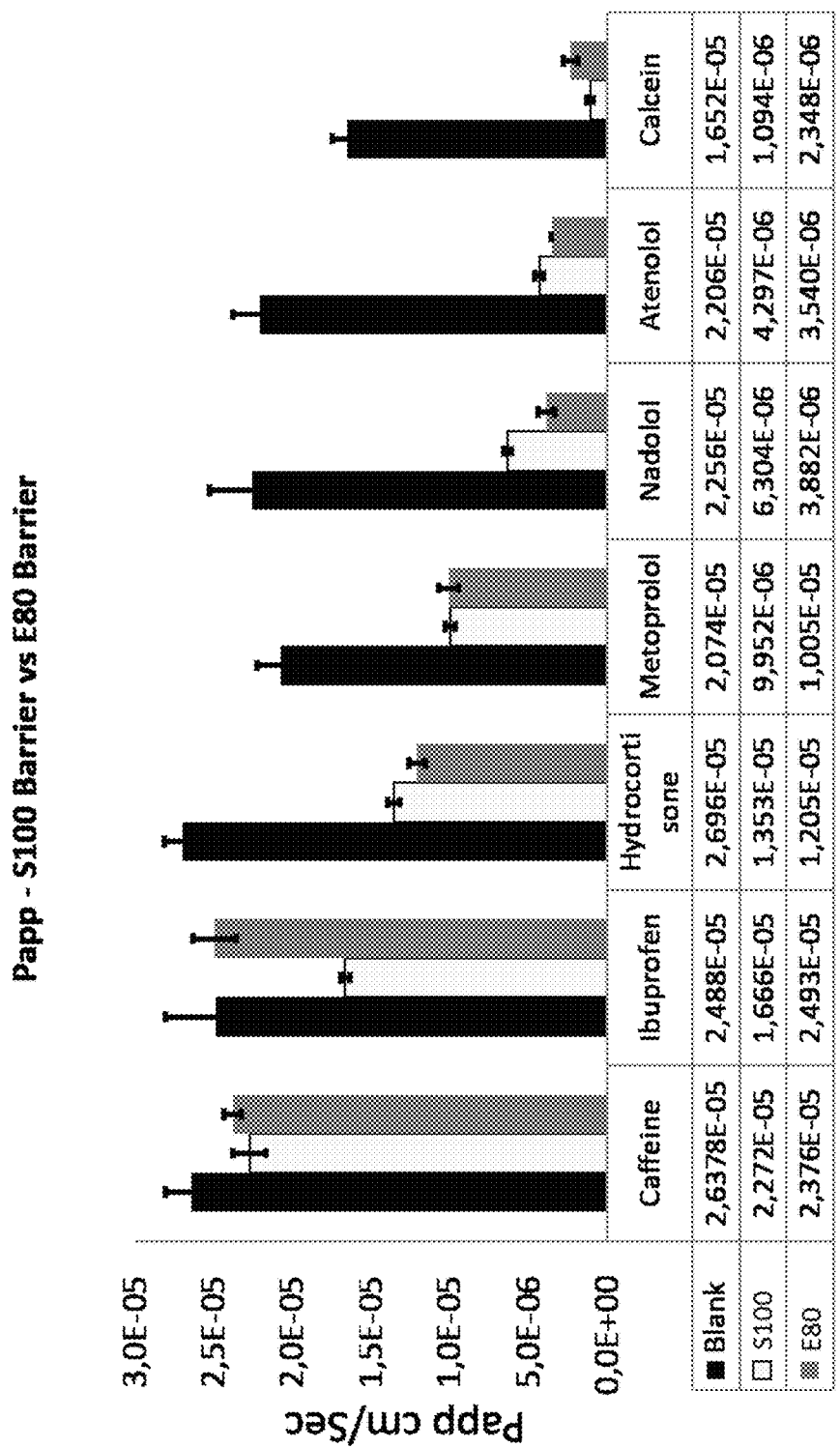
FIG. 5 shows the effect that different lipid composition of the barrier of the present invention has on the permeability of some drugs.

Permeability experiments were carried out similarly to example 1. Results reported in FIG. 5 evidence that the changing in lipid composition has a strong influence on the permeability of at least three compounds (ibuprofen, nadolol and calcein.

This experiment is relevant since it demonstrate that the barrier matter of this patent can be easily modified in order to mimic different relevant biological tissues lipid composition (e.g. intestine, skin, BBB) and enabling the possibility to have more accurate evaluation of drug permeability.

Example 7

One of the biggest issue for the available in vitro assay is their stability in the presence of additives and extreme acidic pH condition (mimicking gastric absorption).

Figure 6:
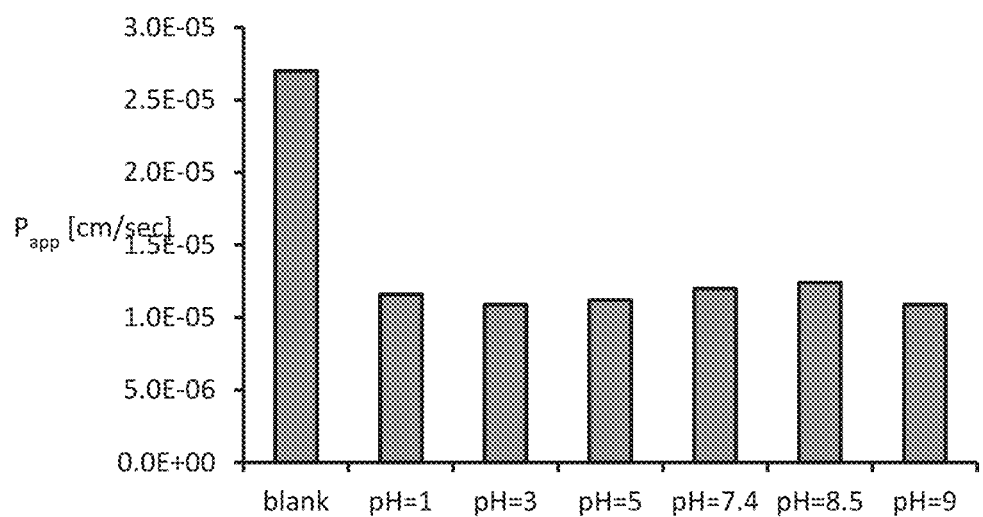
FIG. 6 shows the effect of pH on the integrity and functional stability of the barrier of the present invention.

In order to evaluate if the barrier described in this patent application own sufficient stability at all pH, permeability of model compound hydrocortisone through the barrier was measured similarly to example 1, but at different pH of the media (1, 3, 5, 8.5 and 9). FIG. 6 shows that the permeability of hydrocortisone results almost unaffected by the changing of pH.

If the barrier would be damaged by aggressive pH, an increasing in drug permeability would be expected.

REFERENCES

[1] Amidon G L; Lennernaes H; Shah V P; Crison J R: A theoretical basis for a pharmaceutical drug classification, Pharmaceutical Research (1995), 12(3), 413-20.
[2] Waiver of In Vivo Bioavailability and Bioequivalence Studies for Immediate-Release Solid Oral DosageForms Based on a Biopharmaceutics Classification System" U.S. Food and Drug Administration, Center for Drug Evaluation and Research, August 2000, http://www.fda.gov/downloads/Drugs/GuidanceComplianceRegulatoryInformat ion/Guidances/ucm070246.pdf (latest access Jan. 7, 2013).
[3] Hidalgo I J et al. (1989), Characterization of the human colon carcinoma cell line (Caco-2) as a model system for intestinal epithelial permeability, Gastroenterology 96: 736-49.
[4] http://www.cyprotex.com/admepk/in-vitro-permeability/caco-2-permeability/
[5] http://www.permegear.com/franzatfaqs.htm and http://www.sesanalysesysteme.de/SES Franz Cell dt.htm (latest access Jan. 7, 2013).
[6] Flaten G E, D hanikula, A B, Luthman K, Brandl M. (2006), Drug permeability across a phospholipid vesicle based barrier: A novel approach for studying passive diffusion, European 3. Pharm. Sci. 27: 80-90.
[7] Engesland, A; Skar, M; Hansen, T; Skalko-Basnet, N; Flaten, G E (2013), New applications of phospholipid vesicle-based permeation assay: Permeation model mimicking skin, Journal of Pharmaceutical Sciences 1 02(5): 1588-1600.
[8] CORTI, G. et al. (2006) "Development and evaluation of an in vitro method for prediction of human drug absorption. I. Assessment of artificial membrane composition." EUROPEAN JOURNAL OF PHARMACEUTICAL SCIENCES, 27, 346-353,
[9] Flaten, G. E., A. B. Dhanikula, K. Luthman and M. Brandl (2006). "Drug permeability across a phospholipid vesicle based barrier: A novel approach for studying passive diffusion." *European Journal of Pharmaceutical Sciences* 27(1): 80-90.
[10] Naderkhani, E., J. Isaksson, A. Ryzhakov and G. E. Flaten (2014). "Development of a Biomimetic Phospholipid Vesicle-based Permeation Assay for the Estimation of Intestinal Drug Permeability." *Journal of Pharmaceutical Sciences* 103(6): 1882-1890.
[11] Fischer, S. M., S. T. Buckley, W. Kirchmeyer, G. Fricker and M. Brandl (2012). "Application of simulated intestinal fluid on the phospholipid vesicle-based drug permeation assay." *International Journal of Pharmaceutics* 422 (1-2): 52-58.
[12] Ingels, F., B. Beck, M. Oth and P. Augustijns (2004). "Effect of simulated intestinal fluid on drug permeability estimation across Caco-2 monolayers." *International Journal of Pharmaceutics* 274(1-2): 221-232.

The invention claimed is:

1. A barrier assembly, for determining permeability of one or more chemical compounds across a biological barrier, the barrier assembly comprising:
   a donor compartment for adding the chemical compound or a composition comprising the compound;
   an acceptor compartment for accepting the compound upon permeation across a barrier; and
   a barrier separating the donor compartment and acceptor compartment;
   wherein said barrier comprises on one side a polymeric support, a phospholipid layer adhering to the surface of the polymeric support, and a cover layer on top of the phospholipid layer.

2. The barrier assembly according to claim 1, wherein the thickness of the polymeric support ranges from 0.1-300 μm.

3. The barrier assembly according to claim 1, wherein the thickness of the phospholipid layer ranges from 0.1-300 μm.

4. The barrier assembly according to claim 1, wherein the phospholipid layer is present in an amount of 0.05-10 mg/cm2 on the surface of the polymeric support.

5. The barrier assembly according to claim 1, wherein the polymeric support comprises cellulose, cellulose acetate, cellulose nitrate, cellulose hydrate, hydrophilic mixed cellulose esters, polyamides, polyethylene, polypropylene, polyurethane, polyethylenterephthalate, polyvinylfluoride, polyvinylchloride, polyvinylidendifluoride, polytetrafluoroethylen, polysulfones, a hydrophilic polyethersulfone, polycarbonate, or cellulose hydrate.

6. The barrier assembly according to claim 1, wherein the polymeric support comprises pores that are smaller than 10 nm in diameter.

7. The barrier assembly according to claim 1, wherein the phospholipid layer comprises glycerophospholipids.

8. The barrier assembly according to claim 1, wherein the phospholipid layer comprises glycerolipids.

9. The barrier assembly according to claim 1, wherein the phospholipid layer contains less than 15% (w/w) organic solvent.

10. The barrier assembly according to claim 1, wherein the polymeric support comprises cellulose hydrate and the phospholipid layer comprises phosphatidylcholine.

11. The barrier assembly according to claim 1, wherein the barrier retains its integrity in the presence of surfactants, selected from the group consisting of non-ionic surfactants, polysorbates, Polysorbate 80 or 60, non-ionic solubilsers, Cremophor, Triton-X, bile salts, taurocholate, cholic acid, lithocholic acid, chenodeoxycholic acid, anionic detergents, sodium dodecyl sulfate (SDS), and cetyl trimethylammonium chloride.

12. The barrier assembly according to claim 1, wherein the barrier retains its integrity in concentrations of:
Triton-X of up to 5% (M/M); and/or
SDS up to 10%, and/or DMSO of up to 15%; and/or
Polysorbate 60 or 80 up to 10%; and/or
Polyethoxylated castor oil (Cremophor) up to 10%; and/or
Ethanol up to 10%.

13. The barrier assembly according to claim 1, wherein the barrier retains its integrity in solutions of bio-mimetic media (BMM).

14. The barrier assembly according to claim 1, wherein the barrier comprises two or more alternating layers of polymeric support and phospholipid layer, and a cover layer.

15. The barrier assembly according to claim 1, wherein the donor compartment or the acceptor compartment or both compartments are loaded with a liquid composition comprising:
polysorbate, bile salts, cholic acid, lithocholic acid and/or chenodeoxycholic acid; and/or
non-ionic solubilisers; and/or
surfactants; and/or
anionic detergents; and/or
cationic detergents; and/or
Bio-mimetic media (BMM) solutions; and/or
one or more organic solvents.

16. The barrier assembly according to claim 1, wherein the biological barrier is the human gastro-intestinal barrier, the human blood brain barrier (BBB), nasal, buccal, dermal, rectal, vaginal, ocular, pulmonal, skin, cornea or a vesicular barrier.

17. The barrier assembly according to claim 1, wherein the one or more chemical compounds are drug substances, drug candidates, medical preparations, drug formulations, drugs, food/feed ingredients, food/feed compositions, environmental toxins or bacterial toxins.

18. A method for determining the permeability of one or more compounds across a biological barrier, the method comprising:
providing the barrier assembly according to claim 1;
adding a compound or a composition comprising the compound to the donor compartment of the barrier assembly; and
measuring the amount of the compound permeating into the acceptor compartment.

19. The method according to claim 18, further comprising determining the permeability of the compound.

20. The method according to claim 18, wherein the donor compartment is loaded with a liquid composition comprising:
polysorbate, bile salts; and/or
non-ionic solubilisers; and/or
surfactants; and/or
anionic detergents; and/or
cationic detergents; and/or
Bio-mimetic media (BMM) solutions; and/or
one or more organic solvents.

* * * * *